United States Patent
Watschke (12)

(10) Patent No.: US 6,451,741 B1
(45) Date of Patent: Sep. 17, 2002

(54) INHIBITION OF VEGETATIVE GROWTH

(76) Inventor: Thomas L. Watschke, 614 Berkshire Dr., State College, PA (US) 16803

( * ) Notice: Subject to any disclaimer, the term of this patent is extended or adjusted under 35 U.S.C. 154(b) by 0 days.

(21) Appl. No.: 10/004,745

(22) Filed: Dec. 4, 2001

Related U.S. Application Data

(63) Continuation-in-part of application No. 09/650,505, filed on Aug. 29, 2000, now abandoned.

(51) Int. Cl.$^7$ ................................................ A01N 41/06
(52) U.S. Cl. ...................................................... 504/333
(58) Field of Search .......................................... 504/333

(56) References Cited

U.S. PATENT DOCUMENTS 3,894,078 A * 7/1975 Fridinger .................... 260/501

* cited by examiner

*Primary Examiner*—Alton Pryor
(74) *Attorney, Agent, or Firm*—Duane Morris LLP

(57) ABSTRACT

A method for inhibiting the rate of the growth of vegetation is disclosed, which includes contacting the vegetation with an effective amount of a composition including 5-acetamino-2,4-dimethyltrifluoromethanesulfonanilide and/or ethyl 4-cyclopropyl(hydroxy)methylene-3,5-dioxocyclohexanecarboxylate.

2 Claims, No Drawings

INHIBITION OF VEGETATIVE GROWTH

This application a continuation-in-part of application Ser. No. 09/650,505, filed Aug. 29, 2000 now abandoned.

FIELD OF THE INVENTION

This invention relates to the use of a composition including 5-acetamido-2,4-dimethyltrifluoromethanesulfonanilide and/or trinexapac-ethyl(ethyl 4-cyclopropyl(hydroxy) methylene-3,5-dioxocyclohexanecarboxylate) in a spray foam form. This composition is a plant growth regulator.

BACKGROUND OF THE INVENTION

N-substituted perfluoroalkanesulfonamides are broadly described in U.S. Pat. No. 3,639,474 as active herbicides and plant growth modifiers. 5-acetamido-2-chlorotrifluoromethanesulfonanilide and 5-acetamido-2-methyltrifluoromethanesulfonanilide were particularly disclosed therein to have particular plant growth modifying activity, i.e., as to their ability to retard the growth of grass without significant distortion of the normal foliar shape. This plant growth modifying activity is of interest because it reduces the number of times grass must be mowed.

It has previously been found that a novel derivative of trifluoromethanesulfonanilide, 5-acetamido-2,4-dimethyltrifluoromethanesulfonanilide, is a much more effective grass growth regulator than 5-acetamido-2-methyltrifluoromethanesulfonanilide, the preferred compound of the above mentioned patent. It has been found, both in greenhouse testing and in outdoor testing, that the compounds of the present invention can be used at greatly reduced rates of application. This result is both unexpected and economically desirable.

The invention also includes horticulturally acceptable salts of 5-acetamido-2,4-dimethyltrifluoromethanesulfonanilide, novel intermediates useful for its preparation and processes for the preparation thereof.

DETAILED DESCRIPTION OF THE INVENTION

This invention relates to the use of a composition including the compound 5-acetamido-2,4-dimethyltrifluoromethanesulfonanilide in spray foam form, as well as horticulturally acceptable salts thereof, certain intermediates therefor and processes for the preparation thereof. The compound is useful as a herbicide and plant growth modifier.

It is therefore an object of the invention to provide a composition including the compound 5-acetamido-2,4-dimethyltrifluoromethanesulfonanilide and its horticulturally acceptable salts in spray foam form, suitable for homeowner and industrial use.

The salts of the above compound are prepared by treating the acid form compound with a stoichiometrically equivalent amount of an appropriate base under mild conditions, as described in U.S. Pat. No. 3,894,078, herein incorporated by reference. Among the metal salts of the above compound are alkali metal (e.g., lithium, sodium and potassium), alkaline earth metal (e.g., barium, calcium and magnesium) and heavy metal (e.g., zinc and iron) salts as well as other metal salts such as aluminum. Appropriate bases for use in preparing the metal salts include metal oxides, hydroxides, carbonates, bicarbonates and alkoxides. Some salts are also prepared by transmetallation reactions. The organic amine salts include the salts of alkylamines and aromatic amines, preferably containing not more than ten carbon atoms. These and the ammonium salts can be prepared by reacting the acid form with the appropriate organic base or ammonium hydroxide. The salts of the invention are frequently formed by reacting the precursors in aqueous solution. This solution can be evaporated to obtain the salt of the compound as a dry powder. In some cases, it may be more convenient to use a nonaqueous solvent such as alcohols, acetone, etc. Since many of the salts are water soluble, they are often used in the form of aqueous solutions.

The compositions of the present invention are quite active as preemergence herbicides at rates of application such as 20, 10 and 5 pounds per acre. Good control of nutsedge (Cyperus sp.) is obtained by preemergence application of 2.5 pounds of active ingredient per acre. When applied postemergence as a plant growth regulator, and particularly as a grass growth regulator, it shows high activity at an application rate of 2 pounds per acre and the rate applied may be as low as 0.15 pounds per acre while maintaining control of grass growth.

In order to be used as a plant growth regulator or as a herbicide, the rate of application will vary as taught hereinabove. When the compound is used at low rates it may be toxic to a few weed species, although its primary function is as a grass growth regulator. Of course, it must be safe to the grass species treated at the chosen rate of application.

Whether used as a plant growth regulator or herbicide, the composition of the invention and its salts can be used alone, for example, as dusts or granules of the compounds, or preferably they may be applied in formulations containing the active ingredients in a horticulturally acceptable extending medium including wax bars of various types. The formulations are comprised of one or more active ingredients and one or more adjuvants and/or carriers. Specific formulations are useful to facilitate the application of the compounds and to achieve specific biological objectives such as controlling the availability of the herbicide, improving adherence to plants, and the like, as is well known to those skilled in the art.

The compounds of the invention may be formulated as wettable powders, emulsifiable concentrates, aqueous or nonaqueous solutions and/or suspensions, granules, dusts, wax bars and the like. Said compounds as such can be finely divided and dispersed or suspended in any of the usual aqueous media, or if appropriate salts are used, a solution may be made. Spreading agents, wetting agents, sticking agents or other adjuvants can be added as desired.

When emulsifiable concentrates are prepared the active ingredient can be present in concentration of about 5% to 80% or more, depending upon its solubility in water, but it has been found that the compositions of this invention are preferably used in a concentration of 20 to 50%. The units of concentration are weight per unit weight. When the active ingredients are not in salt form, they are soluble in common organic horticultural solvents such as benzene, toluene, xylene, dichloromethane, chloroform, hexane and heptane or less highly refined aromatic or aliphatic hydrocarbons and mixtures thereof. Examples of these are coal tar fractions, straight run petroleum distillates, thermolytically or catalytically cracked hydrocarbon oil, gas oil, light lubricating oil fractions, kerosene, mineral seal oil, and the like. In appropriate cases, oxygenated solvents such as ketones may be used in or as the carriers. These concentrates can be dispersed in water to permit the use of an aqueous spray. Admixture with a small amount of an organic surface active agent capable of lowering the surface tension of water is preferred, so as to produce more or less stable emulsions.

Examples of surface active agents variously known as dispersing agents, wetting agents or emulsifying agents comprise soft or hard soaps, morpholine or dimethylamine oleate, sulfonated fish, castor and petroleum oils, sodium salts of lignin sulfonic acid, alkylated aromatic sodium sulfonates, such as decylbenzene sodium sulfonate, dodecylbenzene sodium sulfonate, butyl or other amine salts of decyl or dodecylbenzene sulfonic acid, sodium lauryl sulfate, disodium monolauryl phosphate, ethylene oxide condensation products of higher alcohols or higher mercaptans. Mixtures of two or more surface active agents are also feasible. Generally, the surface active agent will comprise only a small proportion of the composition, e.g., 0.1–15% by weight of the toxicant.

The formulation of dry compositions for application as granules, dusts or for further dilution with liquid carriers is readily accomplished by mixing the active compound with a solid carrier. Such solid carriers will be of various sizes from dust to granules. The techniques for such formulations are well known to the art. Suitable carriers include charcoal, talc, clay, pyrophyllite, silicas, fuller's earth, Jime, diatomaceous earth, flours (such as walnut shell, wheat, soya bean, cottonseed and wood flours), magnesium and calcium carbonate, calcium phosphate and the like. Powders may be granulated by the use of suitable binders such as cellulose derivatives, for example ethyl or carboxymethyl, corn syrup, and the like. The compounds of the above formulations are applied by spraying, spreading, dusting or the like.

The rate of application will of course vary, but the compositions of the invention exhibit satisfactory preemergence control of broadleaf and grass weeds at the application rate of about 2 to 20 pounds per acre. As a plant growth regulator, and particularly as a grass growth regulator, activity is obtained at rates as low as one-eighth pound per acre on growing plants. The maximum rate depends upon the sensitivity of the growing plant. For reasons of economy the lowest effective rate is chosen, and for most grasses this will be less than one pound per acre. Local conditions, for example temperature, humidity, wind, precipitation, nature of the soil and the like may require greater or smaller amounts. Effective resolution of these factors is within the skill of those versed in the agricultural art.

The compositions set out hereinabove may contain, in addition to the compositions of the invention, other biologically active substances. Thus, insecticides and fungicides may be incorporated in the compositions. Further, if desired, the compositions may contain fertilizers, trace metals or the like and when applied directly to the soil may additionally contain nematicides, soil conditioners, plant regulators and/or herbicides of similar or different properties.

The compositions of the invention are broadly active as preemergence herbicides. In addition, they also show various types of plant growth modifying activity. Plant growth modification as defined herein consists of all deviations from natural development, for example, defoliation, stimulation, stunting, retardation, desiccation, tillering, dwarfing, regulation and the like. This plant growth modifying activity is generally observed as the compounds of the invention begin to interfere with certain processes within the plant. If these processes are essential, the plant will die if treated with a sufficient dose of the compound. However, the type of growth modifying activity observed varies among types of plants. It has been found that herbicidal activity can be separated from certain other plant growth modifying activity by controlling the rate and the method of application. Of particular interest is the ability to slow the rate of growth of grass.

A preferred compound of the invention, 5-acetamido-2,4-dimethyltrifluoromethanesulfon-anilide, is readily prepared by two methods as disclosed in U.S. Pat. No. 3,894,078.

The reaction may be carried out in suitable non-reactive solvents such as esters of organic acids (e.g., ethyl acetate), amides of organic acids (e.g., N,N-dimethylformamide), ethers (e.g., tetrahydrofuran), chlorinated hydrocarbons (e.g., ethylenedichloride), and the like. It can also be carried out in the absence of solvent.

The reaction temperature may be from about 0° C. to 100° C., depending upon the rate of reaction desired. The reaction proceeds readily at room temperature (about 25° C.).

A solution of the primary arylamine and a substantially equimolar quantity of acid acceptor (such as triethylamine, dimethylaniline, pyridine and the like) in an inert organic solvent is ordinarily used. However, an acid acceptor is not always necessary, and an excess of the primary arylamine may also serve as acid acceptor. Among the suitable solvents are 1,2-dimethoxyethane, ethyl acetate, benzene, chloroform, dichloromethane, dimethylacetamide, dimethylformamide and the like. Alternatively an excess of the primary arylamine may be used or the reaction may be carried out in the absence of solvent. Generally, an equimolar quantity of the trifluoromethanesulfonic anhydride or chloride is added to the solution. The addition is advantageously carried out at −15° C. to 50° C. It is advantageous to allow the reaction mixture to remain at reflux temperature for a few hours following addition. The reaction of Method B may also be carried out in a high pressure reactor. This technique is particularly preferred when the sulfonyl fluoride is used as reactant. The reaction is usually carried out at temperature ranges of 0° to 150° C., but these temperatures may be raised or lowered. Presently preferred is a temperature of about 80° to 100° C. The reaction may be carried out without solvent, or with dimethylformamide, ethyl acetate or excess tertiary amine as solvent, but other advantageous variations are possible.

It will be appreciated that the scope of this invention encompasses a wide range of reaction conditions and the synthetic methods A and B discussed herein are described in general and preferred language. However, a great variation in the use of these synthetic techniques is possible and this invention is broadly inclusive of such variation.

After completion of the reaction, the product is isolated by conventional methods. For example, the reaction mixture can be extracted with excess aqueous sodium hydroxide. The aqueous extract is then washed with organic solvents and treated with charcoal to remove impurities. Subsequent acidification of the aqueous extract with mineral acid then affords the product as a solid which is recrystallized as required to give pure product. When water-soluble solvents are used, the reaction mixture can be poured directly into aqueous mineral acids. The product is then isolated by conventional extraction techniques and purified as above.

Alternatively, 5-amino-2,4-dimethyltrifluoromethanesulfonanilide may be prepared in three steps from 2,4-xylidine. 2,4-xylidine is trifluoromethylsulfonylated to provide the compound 2,4-dimethyltrifluoromethanesulfonanilide by using the general method described hereinabove. Nitration of this intermediate provides the novel intermediate 2,4-dimethyl-5-nitrotrifluoromethanesulfonanilide. Reduction of the nitro compound provides the desired 5-amino-2,4-dimethyltrifluoromethanesulfonanilide.

2,4-Dimethyl-5-nitrotrifluoromethanesulfonanilide is also prepared by the reaction of trifluoromethanesulfonyl fluoride with 5-nitro-2,4-xylidine by using the general method described hereinabove.

In the method of the present invention, the composition may be delivered by any method that produces foam as a carrier, e.g., through an aerosol can, with the can pressured strongly enough to dispense the foam consistently in a downward delivered mode, which provides, e.g., a twelve inch wide band onto the ground. By "foam", it is meant any substance with a consistency similar to that of shaving cream that will dissipate slowly after contact with at the ground (e.g., less than one minute). Concentration levels of composition of about 2% on a volume to volume basis are preferred. As the foam would be highly visible, an individual applying the composition can adjust the width of application, speed of walking, aim, etc., with relative ease. In addition, the "foam" nature of application reduces the possibility of composition drifting away from target areas.

In a preferred embodiment of the present invention, an individual delivering the foam may walk at a speed that maintains the width of the foam at, e.g., six to eight inches, which will assist in providing proper calibration. Improved precision and accurate delivery add to the environmental advantages described above.

In a further preferred embodiment of the present invention, a composition including 5-acetamido-2,4-dimethyltrifluoromethanesulfonanilide and/or trinexapac-ethyl (ethyl 4-cyclopropyl (hydroxy) methylene-3,5-dioxocyclohexanecarboxylate is also effective for inhibiting vegetative growth, also delivered by any method that produces foam as a carrier, as described above.

What is claimed is:

1. A method for inhibiting the rate of the growth of vegetation which comprises contacting said vegetation with an effective amount of a composition consisting essentially of 5-acetamido-2,4-dimethyltrifluoromethanesulfonanilide or ethyl 4-cyclopropyl(hydroxy)methylene-3,5-dioxocyclohexanecarboxylate, or horticulturally acceptable salts thereof, said composition applied to said vegetation in spray foam form.

2. The method as recited in claim 1 which comprises contacting vegetation with an effective amount, less than one pound per acre and as low as one-eighth pound per acre of 5-acetamido-2,4-dimethyltrifluoromethanesulfonanilide or ethyl 4-cyclopropyl(hydroxy)methylene-3,5-dioxocyclohexanecarboxylate, or horticulturally acceptable salts thereof.

* * * * *